US00PP18392P2

(12) United States Plant Patent
Burton

(10) Patent No.: US PP18,392 P2
(45) Date of Patent: Jan. 1, 2008

(54) ***COPROSMA* PLANT NAMED 'TEQUILA SUNRISE'**

(50) Latin Name: *Coprosma*
Varietal Denomination: Tequila Sunrise

(76) Inventor: Stephen Burton, 1896 Hamilton Rd, Cambridge (NZ), 2351

( * ) Notice: Subject to any disclaimer, the term of this patent is extended or adjusted under 35 U.S.C. 154(b) by 0 days.

(21) Appl. No.: 11/452,644

(22) Filed: Jun. 14, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para

(57) ABSTRACT

A new cultivar of *Coprosma* plant named 'Tequila Sunrise' that is characterized by an upright and outwardly spreading habit, leaves that change from green and yellow in the spring to orange and green during the summer to burgundy and brown in the fall and moderate vigor.

1 Drawing Sheet

Botanical classification: *Coprosma*.
Variety denomination: 'Tequila Sunrise'.

BACKGROUND OF THE INVENTION

The present invention relates to a new and distinct cultivar of *Coprosma* plant botanically known as *Coprosma* and hereinafter referred to by the cultivar name 'Tequila Sunrise'.

The new cultivar was discovered by the inventor in a cultivated area of Cambridge, New Zealand in 2003. 'Tequila Sunrise' was discovered as a naturally occurring branch mutation of *Coprosma* 'Yuanne' (not patented).

Asexual reproduction by tip cuttings of the new cultivar 'Tequila Sunrise' was first performed in 2003 in Cambridge, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Coprosma* cultivar 'Tequila Sunrise'.

1. *Coprosma* 'Tequila Sunrise' exhibits an upright and outwardly spreading habit.
2. *Coprosma* 'Tequila Sunrise' exhibits leaves that change from green and yellow in the spring to orange and green during the summer to burgundy and brown in the fall.
3. *Coprosma* 'Tequila Sunrise' exhibits moderate vigor.

The closest comparison cultivars are *Coprosma* 'Evening Glow' (not patented) and 'First Burst' (U.S. Plant Pat. No. 14,906). The new cultivar 'Tequila Sunrise' is distinguishable from 'Evening Glow' by the following characteristics:

1. 'Tequila Sunrise' has leaves that are more orange during the summer than 'Evening Glow'.
2. 'Tequila Sunrise' has leaves that are more burgundy and brown during the winter than 'Evening Glow'.
3. 'Tequila Sunrise' has slightly wavy leaves. The leaves of 'Evening Glow' are flat.

The new cultivar 'Tequila Sunrise' is distinguishable from 'Fire Burst' by the following characteristics:

1. 'Tequila Sunrise' has longer leaves than 'Fire Burst'.
2. 'Tequila Sunrise' has leaves that are more orange during the summer than 'Fire Burst'.
3. 'Tequila Sunrise' has leaves that are more burgundy and brown during the winter than 'Fire Burst'.

Plants of the new cultivar 'Tequila Sunrise' are distinguishable from the parent plant 'Yuanne' by the following characteristics:

1. 'Tequila Sunrise' has leaves that are more orange during the summer. The leaves of 'Yuanne' are greener during the summer.
2. 'Tequila Sunrise' has leaves that are burgundy and brown during the winter. The leaves of 'Yuanne' are dark brown.
3. 'Tequila Sunrise' has a smaller overall size than 'Yuanne'.

BRIEF DESCRIPTION OF THE DRAWING

The accompanying photograph illustrates the distinguishing traits of *Coprosma* 'Tequila Sunrise'. The plant in the photograph shows an overall view of a 12 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Coprosma* cultivar named 'Tequila Sunrise'. Data was collected in Cambridge, New Zealand from 12 month old outdoor grown plants in 2.5 liter containers. The time of year was Fall and the average temperature range was 18 to 25 degrees Centigrade during the day and 12 to 20 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species. 'Tequila Sunrise' has not been tested under all possible conditions and phenotype differences may be observed with variations in environmental, climatic, and cultural conditions, however, without any variance in genotype.

Botanical classification: *Coprosma* 'Tequila Sunrise'.
Use: Ornamental perennial.
Parentage: 'Tequila Sunrise' is a naturally occurring branch mutation of *Coprosma* 'Yuanne'.
Vigor: Moderate.
Growth rate: Moderate.
Growth habit: Freely branching, dense, bushy habit.
Plant shape: Broad upright inverted triangle.
Suitable container size: 2.5 liter container.
Height: Average 1.0 m in height.
Width: Average 1.0 m in width.
Hardiness: Tolerant to −3 degrees Centigrade.
Propagation: Tip cuttings.
Time to initiate roots: Approximately 20 days in the Summer and 25 days in the Winter.
Time to produce a rooted cutting: Approximately 40 days in the Summer and 200 days in the Winter.
Root system: Fine and fibrous.
Lateral branches:
*Quantity.*—Approximately 20.
*Strength.*—Strong.
*Pinching.*—Yes, at 50 days.
Foliage:
*Texture.*—Smooth, glossy.
*Leaf arrangement.*—Opposite.
*Leaf attachment.*—Sessile.
*Compound or single.*—Single.
*Leaf shape.*—Obovate.
*Leaf apex.*—Obtuse.
*Leaf base.*—Rounded.
*Leaf length.*—Average 3.5 cm in length.
*Leaf width.*—1.6 cm in width.
*Pubescence.*—Absent.
*Leaf margin.*—Entire, unevenly recurved, slightly wavy.
*Vein pattern.*—Pinnate.
*Young leaf color* (*upper surface*).—143A surrounded by 15A, toward margins 24B.
*Young leaf color* (*lower surface*).—Between 144B and 144D.
*Mature leaf color* (*upper surface*).—Center between 137A to 139B, surrounded by 40B, toward margins 43B.
*Mature leaf color* (*lower surface*).—Between N25A to 26A.
*Durability of foliage to stress.*—Moderate to high.
Flowers: Flowers have not been observed.
Disease and insect resistance: Plants of the new *Coprosma* have not been observed for disease or insect resistance.

It is claimed:

1. A new and distinct variety of *Coprosma* plant named 'Tequila Sunrise' as described and illustrated.

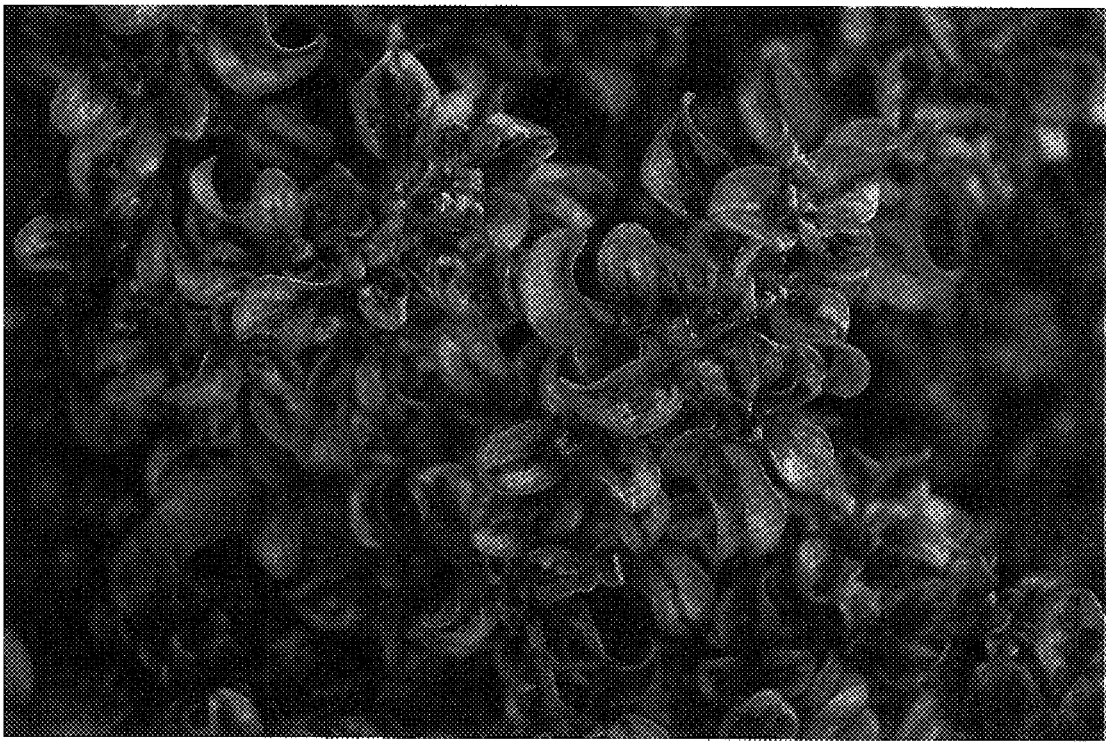

* * * * *